United States Patent [19]

Frei et al.

[11] 4,335,724
[45] Jun. 22, 1982

[54] SOLARIUM

[76] Inventors: Hans-Joachim Frei, Erlenbruchweg 1, 6486 Brachttal 3; Karl Wolf, Ludwigstr. 61, 6450 Hanau 7, both of Fed. Rep. of Germany

[21] Appl. No.: 113,360

[22] Filed: Jan. 18, 1980

Related U.S. Application Data

[62] Division of Ser. No. 872,386, Jan. 26, 1978, abandoned.

[30] Foreign Application Priority Data

| Jan. 26, 1977 [DE] | Fed. Rep. of Germany ... 7702074[U] |
| Apr. 9, 1977 [DE] | Fed. Rep. of Germany ... 7711270[U] |
| Nov. 9, 1977 [DE] | Fed. Rep. of Germany ... 7734341[U] |

[51] Int. Cl.³ .............................................. A61N 5/06
[52] U.S. Cl. .................................... 128/395; 128/396; 128/373; 128/376
[58] Field of Search ............... 128/372, 373, 376, 395, 128/396

[56] References Cited

U.S. PATENT DOCUMENTS

| 709,696 | 9/1902 | Brueck | 128/373 |
| 2,240,819 | 5/1941 | Waly | 128/373 |
| 2,300,008 | 10/1942 | Riess et al. | 128/395 |
| 2,667,169 | 1/1954 | Kambovrakis | 128/372 |
| 2,676,596 | 4/1954 | Rovat | 128/373 |
| 3,170,172 | 2/1965 | Kessman | 128/372 |
| 3,271,786 | 9/1966 | Joy | 128/372 |
| 3,877,437 | 4/1975 | Maitan et al. | 128/373 |
| 3,986,513 | 10/1976 | Stuhl | 128/373 |
| 4,011,874 | 3/1977 | Segawa et al. | 128/372 |
| 4,200,360 | 4/1980 | Mutzhas | 128/372 |

*Primary Examiner*—Robert W. Michell
*Assistant Examiner*—C. W. Shedd
*Attorney, Agent, or Firm*—Friedman, Goodman & Teitelbaum

[57] ABSTRACT

A solarium, especially for medical purposes, having one or more fluorescent tubes mounted in a frame, wherein the frame is constructed as part of a piece of residential furniture, such as a bed, a couch, a seat, a commode, a cabinet, a stand, a lamp, a television set and the like. The fluorescent tubes are disposed in reflectors which are open to an irradiation side of the frame. The fluorescent tubes are mounted under a covering which is permeable to ultraviolet rays. The covering provides a concave longitudinal trough adapted to fit the body of the user. Preferably, at least one solarium lamp is positioned at a distance above the cover so that the user can be irradiated simultaneously on both sides of his body. The solarium may be constructed as a mirror part of a hair dressing cabinet commode. In another embodiment, the fluorescent tubes are bent into a circle, where tubes of different diameters are arranged concentrically to one another. The concentric tubes may be mounted in a bowl-shaped casing, a commercial-type television set and the like.

5 Claims, 11 Drawing Figures

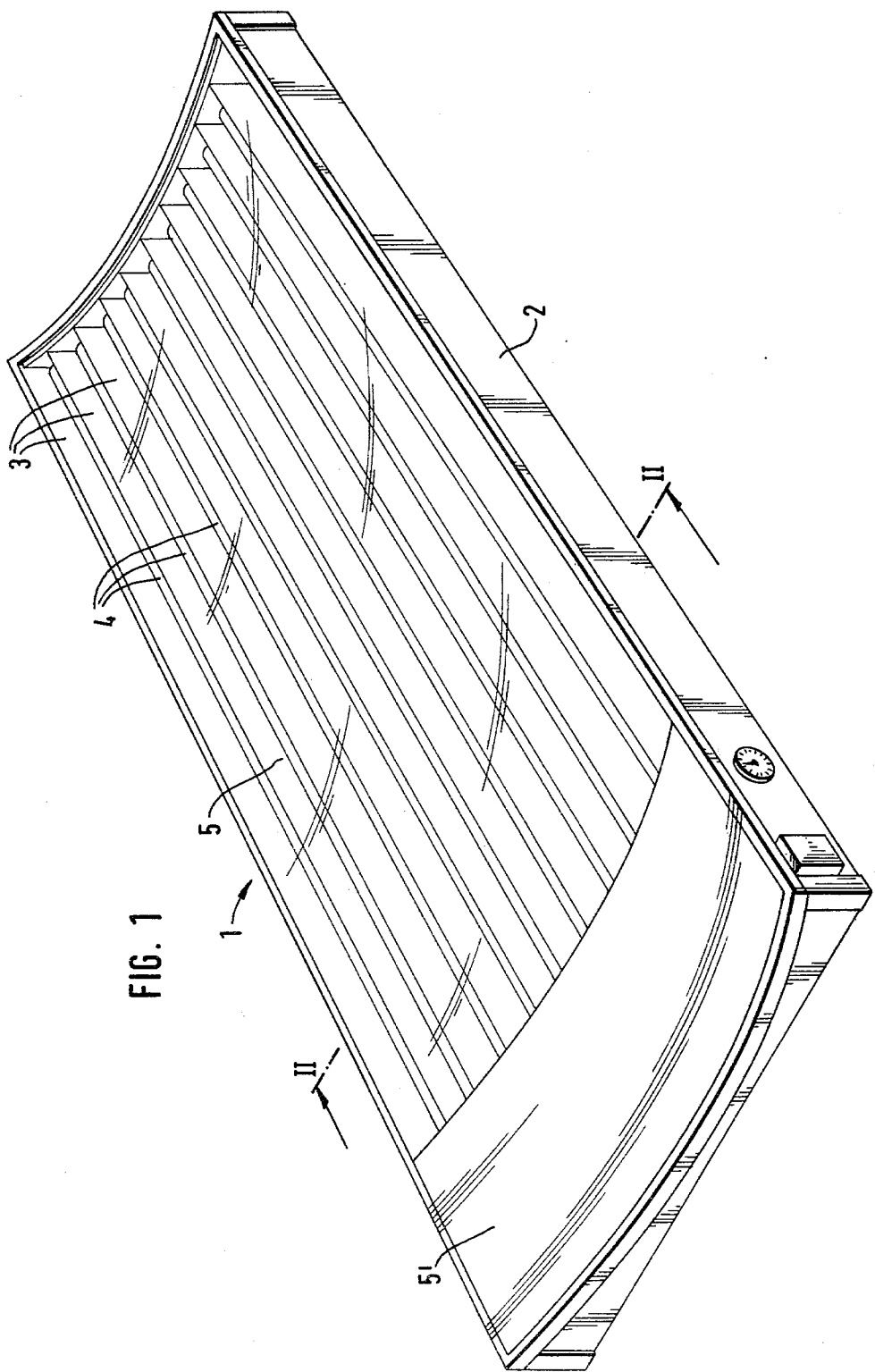

SOLARIUM

This is a division of application Ser. No. 872,386 filed Jan. 26, 1978 now abandoned.

The present invention relates to a solarium, especially for medical purposes, in which one or more ultraviolet fluorescent tubes are held in a frame or casing, which frame or casing permits at least one-sided emergence of ultraviolet radiation upon the person to be treated.

An object of the present invention is to provide a solarium which can be versatilely usable, especially in a residential home, and which can be as space-saving as possible.

This above object is achieved, according to the present invention, by means of the frame or the casing being formed as part of an article of residential furniture, for example a bed, a couch, a seat, a commode, a cabinet, a stand, a radiation apparatus, a lamp or a television set.

In a further development of this solarium, there are allocated to ultraviolet fluorescent tubes, one or more reflectors open toward the irradiation side. The reflectors receive or partly surround the ultraviolet fluorescent tubes. Thus, the radiation intensity in the desired zone can be increased and, if need be, also regulated.

Further, the ultraviolet fluorescent tubes may be positioned for protection under a covering which is permeable to ultraviolet rays in a partial zone. This covering, especially in the case of a horizontal arrangement, can be held in the frame or casing as a rest for the user. Such a solarium can further be improved by increasing the convenience for the user and by broadening the range of its effect. This improvement can be realized by means of forming the covering as a concave longitudinal trough which is substantially adapted to the body form of the user, being adaptable thereto or adapting itself in use. Through the substantially concave form of the longitudinal trough, the lying of the user on the solarium according to the present invention is more comfortable. Furthermore, the incidence of rays takes place from a large range of angles of incidence if the ultraviolet fluorescent tubes are arranged on a concave surface corresponding essentially to the longitudinal trough, whereby the degree of utilization and thereby the useful value of the solarium is substantially improved.

The covering may include various solid, deformable and yielding materials. Thus, the covering preferably can be fabricated from a thermoplastic material that is more or less yielding under the action of the heat given off by the fluorescent tubes and under the pressure of the body of the user resting on it, and thereby the covering can fit itself to the body form of the user. The solarium of the present invention, therefore, in a couch for example, offers in every case a comfortable shape for different users of differing body form. The covering may, in particular, be of flexible material and be deformed only under the pressure of the user's body resting on it. Solariums are well known, wherein the ultraviolet light emitting sources and the covering materials which are permeable to the ultraviolet light are well known to a person skilled in the art, see U.S. Pat. No. 4,095,113 to which reference may be made.

An especially space-saving feature of the solarium of the present invention is achieved by means of the frame being formed and dimensioned in such a way that it is installable in a part of a piece of residential furniture, preferably a bed, sofa or seat.

In the event that the solarium is to form the seating surface and back of a seat, it is constructed in two parts where the frame is adapted to the seating surface and back recess of the frame of the seat.

The covering may take the form of a matress or a seat cushion. If the solarium is then formed as a bed, sofa or seat inset, it is only necessary to remove the corresponding sheet or the corresponding cover and the solarium of the present invention is ready for operation, without the solarium otherwise occupying a special place, which would be troublesome especially in close quarters. Simultaneously, the user is offered increased comfort in use thereof through such formation of the covering as a matress or seat cushion.

In order to heighten the effect of the beams in all directions, the covering can also be formed as a tube which is turnable about its longitudinal axis or which is swingable back and forth in a desired rhythm, the covering being preferably of Plexiglas. The user can lie down in this tube and, in the case of complete rotation, buckle himself in securely. In this manner, there can be achieved an action of rays from all sides and a uniform tanning of the user.

In the known prior art solarium, the face of the user is not included in the irradiation, and this is considered to be a disadvantage thereof. This situation is solved in the present invention by lamp means disposed at a distance over the covering, preferably in the head region. Accordingly, one or more solarium lamps are provided, being shorter in comparison with the body size of the user, the lamps being directed essentially downward. If this separate solarium lamp is arranged stationarily at the head region, the user, while he is lying with his back on the covering of the solarium, can simultaneously have his face treated with ultraviolet radiation.

However, the separate solarium lamp, at least one in number, can also be movable in a longitudinal direction over the covering, possibly with variable speed, so that when the user is lying, for example with his back on the covering of the solarium, he can be exposed over the entire front side of his body, inclusive of his face, simultaneously and uniformly to the ultraviolet radiation.

A further variation possibility of the solarium lamp or lamps arranged separately over the covering, is that several of these solarium lamps can be arranged on a circular arc spanning the width of the covering, with the beam direction having an angular spacing to face the longitudinal axis of the longitudinal trough. In this manner the face or, if need be, the body of the user is irradiated not only directly from above, but also obliquely from the sides.

In order to achieve this above effect, a solarium lamp can also be movable on the circular arc over the covering with a particular alignment of the beam direction upon the longitudinal axis of the longitudinal trough, where the solarium lamp is moved back and forth, for example with the aid of a time control, over this circular arc.

The frame part of the solarium, which serves for the support of the user, normally has a total approximate length that corresponds to the body size of a human being. In order to make the entire apparatus less expensive it is possible, however, to provide that the covering retains the dimension required for the support of the user, but that under this covering, such as for example plexiglass, a solarium element substantially shorter in length is movable in the longitudinal direction of the covering, if need be, with a time control having an adjustable variable speed. In this manner, simultaneously, the effective irradiation intensity can be varied. The shorter solarium element is similar to the above mentioned solarium lamp which moves back and forth over the user.

In the last-discussed case it is possible, for example, for the covering of the solarium, which serves for the support of the user, to be constructed as a hammock, the weave of which may consist of a material substantially permeable to ultraviolet radiation. The covering is preferably toned or colored or opaque glass or glass-like material, so that the ultraviolet fluorescent lamps remain invisible.

In one further development, the solarium has a self-supporting chassis.

In order to make it possible to provide the solarium with an appearance of a piece of furniture, it can be provided with applicable masking elements, such as wood, appliable without special tools.

In order to facilitate the user in rising from a solarium formed as a couch, the solarium may have on one or more of its sides, or possibly all around, a grip strip.

The solarium can have a covering designed in form and size for the support of several persons, and therefore, for example, be provided with several longitudinal troughs.

The solarium can also be supplied for another purpose by forming it as the mirror part of a hairdressing cabinet or a hairdressing commode. Conversely, the hairdressing cabinet or the hairdressing commode formed according to the present invention offers a space-saving feature possibility for the desired solarium. Thus, no special space requirement is necessary for the solarium since it is accommodated in the hairdressing cabinet or hairdressing commode which is needed in any case in a residential home.

The reflectors and fluorescent tubes forming the solarium are preferably provided in the stationary middle portion of the mirror part.

The reflectors and fluorescent tubes can be arranged behind the mirror plates which are mounted laterally and can be shiftable or swingable away from the stationary mirror part. In the use of the hairdressing cabinet or hairdressing commode as a piece of furniture for hairdressing, the mirror plates lie in front of the reflectors and fluorescent tubes, so that these are covered and therefore invisible. The outer appearance of the hairdressing cabinet or hairdressing commode corresponds to the usual piece of furniture of this type. If the mirror plates or plate are then shifted to the side or swung away, the reflectors and fluorescent lamps are exposed and the piece of furniture can be used as a solarium.

The reflectors and fluorescent tubes may, however, also be mounted, for example, in the back wall of the hinged side wings of the mirror part. When the side wings are folded shut, the hairdressing cabinet or hairdressing commode corresponds in its appearance to the usual pieces of furniture of this type, i.e., when the front surface of the side wings in each case and also the stationary middle part are provided with mirror plates, such a cabinet corresponds to the toilet cabinets ordinarily set up or hung in bathrooms. Thus, by swinging open the side wings and, possibly, also by lateral shifting of the mirror plate or plates of the stationary middle part, the hairdressing cabinet or the hairdressing commode can then be used as a solarium, with also the possibility of lateral irradiation.

In the same or a similar manner, bedroom cabinets can also be equipped with a solarium. If, for example, the inner surfaces of two adjacent cabinet doors, which are outwardly openable in each case away from each other, are equipped with solariums, the user by opening the two cabinet doors can place himself in the interspace formed therebetween for solarium irradiation.

In solariums known in the prior art, there have been used rod-form tubes, therefore straight fluorescent tubes. Thus, there is established a rectangular zone from which the ultraviolet radiation proceeds. This restriction is likewise to be obviated with the proposed present invention.

For this above reason, the fluorescent tubes have been bent into a circle or virtually into a circle. Such fluorescent tubes permit the creation of a round field of radiation of uniform radiation density, which is desirable for various technical reasons, but also for esthetic reasons.

These circular tubes can also be arranged concentrically to one another or in one another by using several circularly bent fluorescent tubes of different diameters in order to achieve the uniform radiation intensity. Also restrictions of the field of radiation can be obtained by switching on, for example, only the innermost fluorescent tube and thereby irradiating a restricted zone.

The bent fluorescent tubes can be simply accommodated in a bow-shaped casing which is suited as a part of a piece of furniture, and also as an apparatus part of irradiation installations, hairdressing salons, launderettes and the like.

The effective radiation intensity is increased if the inner surface of the casing is formed of a radiation-reflecting coating, or to each fluorescent tube there is individually allocated a reflector with a form adapted to the curvature of the fluorescent tube.

The versatility of utilization of the casing provided with the circularly bent fluorescent tubes is yielded from the alternative manners of mounting, for example, on a pedestal or stand, on a pivot arm arrangement or an adjustable ceiling suspension.

An especially space-saving embodiment of the solarium as a home solarium is achieved if the fluorescent tubes are accommodated in the casing of an available television set.

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 shows schematically in an oblique view a solarium according to the present invention having a covering in the form of a solid concave longitudinal trough;

Figure 1A:
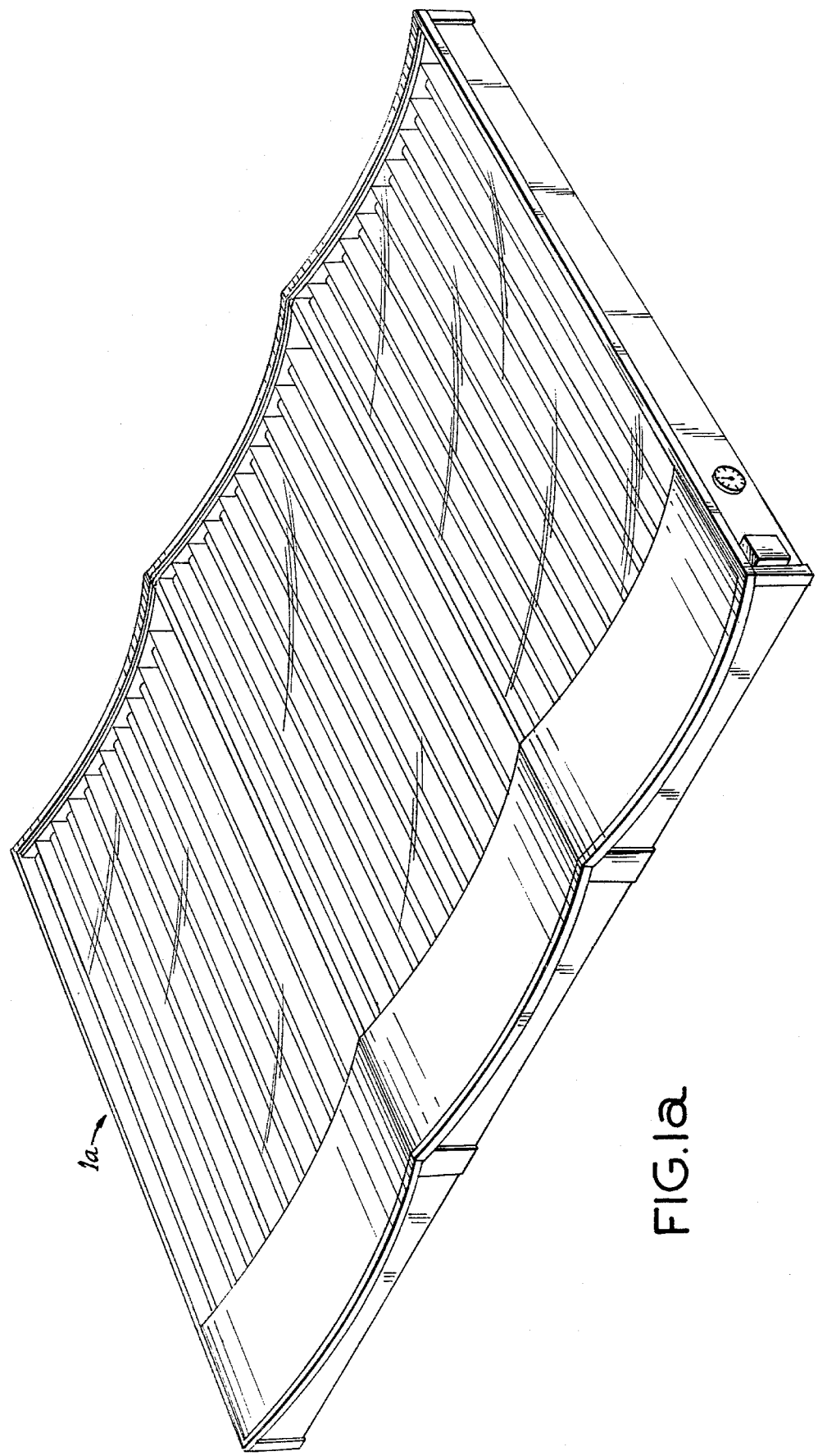
FIG. 1a shows schematically in an oblique view a solarium according to the present invention having several longitudinal troughs.

As shown in FIG. 1, the solarium 1 according to the present invention has a surrounding frame or casing 2 which is dimensioned in such a way that the area determined by it corresponds approximately to the body size of a human being. In the frame 2, reflectors 3 are supported adjacently to one another. The reflectors 3 open upward and run in the longitudinal direction of the frame 2, the reflectors 3 being fabricated preferably of aluminum. The upward-facing longitudinal openings of the reflectors 3 occupy, except for a covered head section 5', virtually the entire surface of the solarium 1. Within the reflectors 3 are mounted ultraviolet fluorescent tubes 4.

Figure 2:
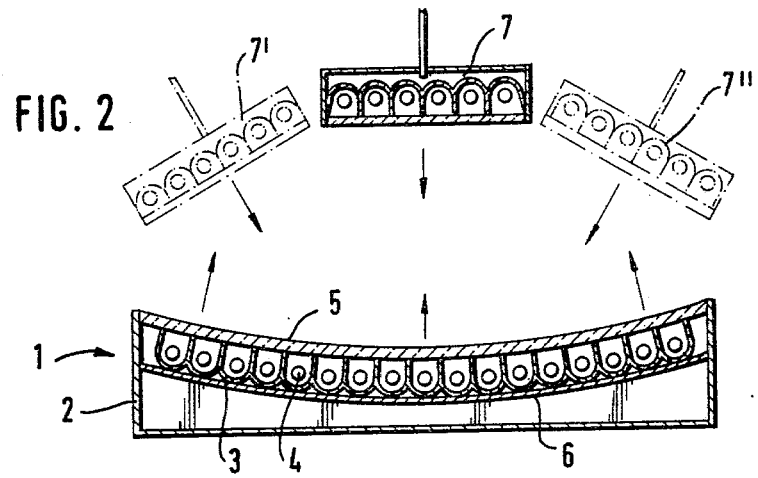
FIG. 2 shows a section taken along the line II—II of FIG. 1 provided with a separate solarium element arranged at a distance above the covering, the separate solarium element being swingable in an arc.

Over the reflectors 3 and fluorescent tubes 4, a covering 5 is supported in the frame 2. The covering 5 is substantially permeable to ultraviolet radiation in the region for supporting the body of the user. The head zone of the covering is provided with the section 5' which is impermeable to radiation. The covering 5, inclusive of the head section 5', is formed as a concave trough, in which the user can lie down. FIG. 1 shows a relatively slight curvature of the trough. The curvature can obviously be increased as much as desired, so that the user is enclosed by more or less of an angular range, where the user is irradiated from the entire angular range which is provided in the solarium. FIG. 1a shows a solarium 1a, according to the present invention, having a covering designed in form and size for the support of several persons, and therefore, for example, being provided with several longitudinal troughs. As shown in FIG. 2, the reflectors 3 with the ultraviolet tubes 4 are arranged on a concave surface 6 corresponding to the curvature of the covering 5.

In order to make it possible to also irradiate the user's face simultaneously with the radiation of his body, a solarium element shown in FIG. 2 is mounted above the head section 5'. The solarium element 7 is short in comparison to the length of the frame 2, and can be swung to change its angle for different lateral positions, as indicated by the broken line positions 7' and 7". In addition to the middle solarium element 7, in order to provide the corresponding side positions and oblique settings thereof, there can be provided separate solarium elements 7' and 7" on each side as indicated in FIG. 2. It is also possible, however, to construct the separate solarium elements 7, 7' and 7" as a single unit similar to the solarium 1 in order to serve likewise as a concave-curved solarium at a distance over the resting place. Furthermore, there can be a stationary arrangement of the solarium element or elements 7 (7', 7") extending over the solarium with respect to the longitudinal direction of the solarium 1, being positioned not only over the head section 5', but being also positioned substantially over the entire length of the solarium, or they may just be movably positioned over the longitudinal direction of the solarium 1, which can be achieved with a time control device.

Figure 3:
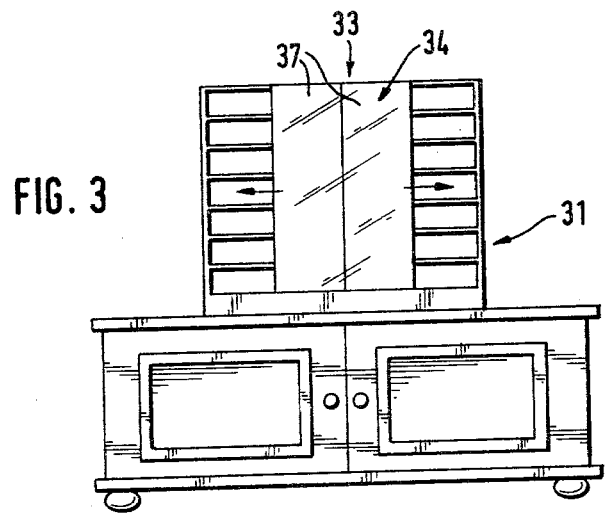
FIG. 3 shows schematically a hairdressing commode according to the present invention.

The hairdressing commode 31 shown in FIG. 3 has a conventional lower cabinet part and an upper superstructure formed as a mirror part 33. The middle piece 34 of the mirror part 33 is provided with a divided mirror plate 37. On both sides of the mirror plate 37, the mirror part 33 is equipped, for example, with compartments. The mirror plate parts 37 can be shifted laterally in the direction of the arrows. Then there is exposed a solarium equipped with reflectors and ultraviolet fluorescent tubes which were disposed behind the mirror plate 37 in the middle piece 34. This exposed solarium is similar to the solarium shown in FIG. 4 which is described below.

Figure 4:
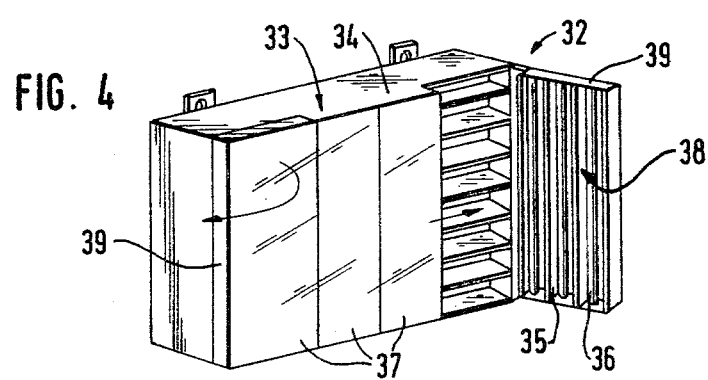
FIG. 4 shows in an oblique view a hairdressing cabinet according to the present invention.

FIG. 4 illustrates another variant of the present invention. As shown, a suspendable hairdressing or toilet cabinet 32 is formed as a whole mirror part 33. The middle piece 34 is similar to the above form shown in FIG. 3, being provided with laterally slidable mirror plate parts 37. On both side borders there are hinged openable side wings 39, in the back wall 38 of which in each case there is provided the reflectors 35 and fluorescent tubes 36 of the solarium. Also, in the stationary middle portion 34 of the hairdressing or toilet cabinet 32, there is arranged a solarium behind the mirror surfaces 37 having reflectors and fluorescent tubes, in a similar arrangement as set forth above in the solarium of FIG. 3, where the reflectors and fluorescent tubes are arranged the same way as the reflectors 35 and fluorescent tubes 36 in the back wall 38. In the closed position of the cabinet 32, the entire front surface is provided with the mirror plates 37.

After folding or swinging open the side wings 39 and laterally shifting away the mirror plates 37 from the fixed middle portion 34, the user can be irradiated from a very large angular range, being exposed both from the front and also from the sides. When the cabinet 32 is suspended on the wall in a usual manner as represented, the cabinet 32 has a relatively short height, where only the head region of the user can be exposed to the solarium radiation. However, the hairdressing or toilet cabinet 32 can obviously also have a height that corresponds to the entire height of a human being, so that a total body irradiation is possible.

According to another form of the present invention represented in FIGS. 5 to 9, the solarium 51 has a frame or casing 52 in an interior space in which there are arranged ultraviolet fluorescent tubes 53, 53', 53", each being bent into a circle. Each circular ultraviolet tube has allocated to it a reflector 54, 54', 54" of corresponding circular form which is disposed behind the ultraviolet fluorescent tubes 53, 53', 53" respectively. The reflectors 54, 54', 54" have, therefore, a channel form, where the individual channels are joined to one another and thus form a common reflector body. The casing 52 is bowl-shaped and opened at one side, from which the ultraviolet radiation can emerge. The casing 52 is swingably mounted on a pedestal or stand 55, i.e., turnable both about the vertical axis and also adjustable in the angle of inclination, so that the ultraviolet radiation can be given off in differing directions.

Figure 5:
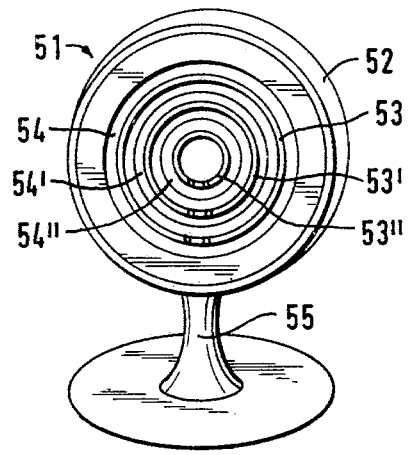
FIG. 5 shows schematically an oblique front view of a solarium according to the present invention provided with a bowl-shaped casing.
Figure 6:
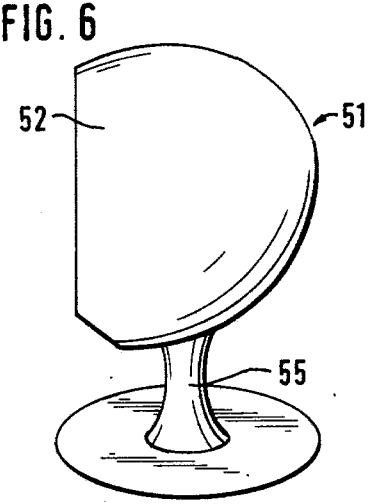
FIG. 6 shows a side view of the solarium of FIG. 5.
Figure 7A:
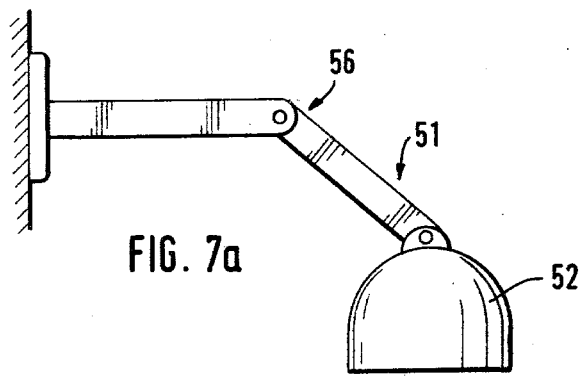
FIGS. 7a and 7b show an arrangement of a solarium casing on a swinging arm mounting according to the present invention.
Figure 7B:
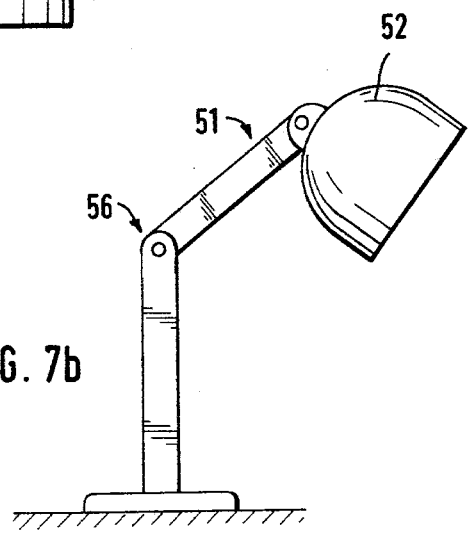

According to FIGS. 7a and 7b, the casing 52 is provided according to the present invention with the ultraviolet fluorescent tubes 53, 53', 53" of different diameters arranged concentrically one within another as shown in FIG. 5. The casing 52 of FIGS. 7a and 7b is mounted on a swinging arm arrangement 56. Such latter arrangement is suited, for example, for use in a beauty parlor.

Figure 8:
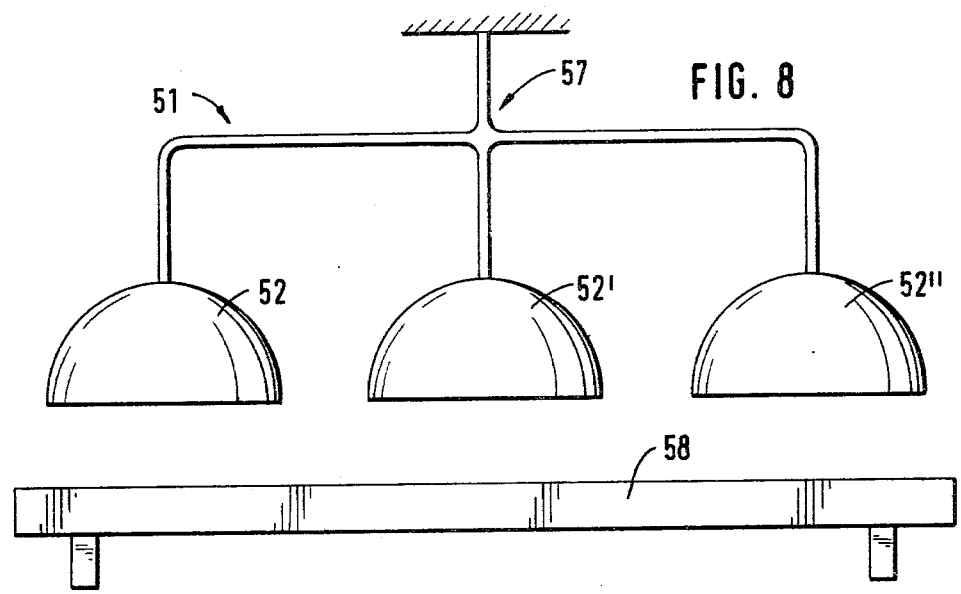
FIG. 8 shows a mounting of several solarium casings on a ceiling fixture over a couch according to the present invention.

FIG. 8 illustrates a ceiling suspension 57 for various similar bowl-shaped casings 52, 52', 52" as described above, which can be arranged, for example, in a solarium installation allocated to a sauna over a couch 58.

Figure 9:
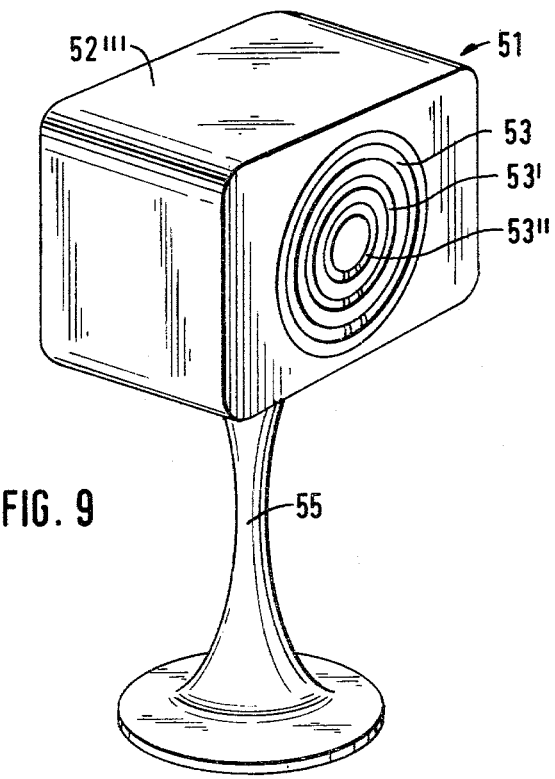
FIG. 9 shows an arrangement of fluorescent tubes according to the present invention provided at the back of a commercial-type television set to form a solarium.

FIG. 9 illustrates a space-saving accommodation of the circular ultraviolet fluorescent tubes 53, 53', 53" as described above, formed according to the present invention in the back of a commercial-type television set having a casing 52'''.

Various other examples for the accommodation for a circle of bent fluorescent tubes can be added within the scope of the present invention.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. Solarium comprising:
   a frame having a longitudinal direction, said frame including body means constructed as part of a piece of residential furniture, one side of said frame being open;
   a plurality of reflectors being supported adjacent to one another in said frame, said reflectors being open towards said one side of said frame and extending in the longitudinal direction of said frame;
   a plurality of ultraviolet fluorescent tubes being mounted in said frame, one of said ultraviolet fluorescent tubes being disposed in each respective one of said reflectors;
   means disposed over said one side of said frame for permitting emergence of ultraviolet radiation from said tubes onto a person disposed on said frame, said means including a covering mounted on said frame above said tubes for supporting the person, a major portion of said covering being permeable to ultraviolet rays directed to the person's body, and a head zone of said covering being impermeable to the ultraviolet rays, said covering providing a concave longitudinal trough for receiving the person; and
   a support member having a concave longitudinal surface disposed in said frame for supporting said reflectors with said tubes therein in a concave arrangement corresponding to said concave longitudinal trough defined by said covering.

2. Solarium according to claim 1, wherein said covering consists of a thermoplastic synthetic material.

3. Solarium according to claim 1, wherein said covering consists of flexible material.

4. Solarium according to claim 1, wherein said frame is a self-supporting chassis.

5. Solarium according to claim 1, wherein said covering is provided with support means having a shape and size for resting several persons thereon.

* * * * *